| United States Patent [19] | [11] Patent Number: 5,069,707 |
| Takeba et al. | [45] Date of Patent: Dec. 3, 1991 |

[54] METHOD FOR REGULATING THE FLOWERING OF PLANTS AND FLOWERING REGULATORS OF PLANTS

[75] Inventors: Go Takeba, Otsu; Osamu Tanaka, Jyoyo, both of Japan

[73] Assignee: Ajinomoto Co., Inc., Tokyo, Japan

[21] Appl. No.: 492,914

[22] Filed: Mar. 13, 1990

[30] Foreign Application Priority Data

Mar. 13, 1989 [JP] Japan ................... 1-060064

[51] Int. Cl.$^5$ ............... A01N 57/00; A01N 43/48
[52] U.S. Cl. ........................... 71/86; 71/92; 71/103; 71/113; 71/115
[58] Field of Search ............ 71/115, 86, 92, 103, 71/113

[56] References Cited

PUBLICATIONS

Sigma, 1991 catalog, St. Louis, Sigma Chemical Company, pp. 360, 977, and 1063–1064.
Chemical Abstracts 77(15):97458f.
Ishizuka et al., "Effect of Bestatin on Mouse Immune System and Experimental Murine Tumors", The Journal of Antibiotics, vol. XXXIII, No. 6, Jun. 1980, pp. 642–652.

*Primary Examiner*—Allen J. Robinson
*Assistant Examiner*—John D. Pak
*Attorney, Agent, or Firm*—Oblon, Spivak, McClelland, Maier & Neustadt

[57] ABSTRACT

The flowering of plants can be regulated by treating the plants with a protease inhibitor, such as, e.g., elastinal, bestatin, diisopropylfluorophosphoric acid (DFP), and CTAH. The protease inhibitor may be applied in the form of a composition, and the method is useful to control the harvesting time of flowering plants.

6 Claims, No Drawings

METHOD FOR REGULATING THE FLOWERING OF PLANTS AND FLOWERING REGULATORS OF PLANTS

BACKGROUND OF THE INVENTION

1. Field of the Invention

The present invention relates to a method for regulating the flowering of plants, by treating plants with a protease inhibitor, and flowering regulators of plants.

2. Discussion of the Background

In agriculture, the process of cultivating, flowering and fruiting plants is a process directly affecting their yield and is also a process which is important for determining their commercial value. In the case of grains, fruits, vegatables or decorative flowering plants, there is a harvest after flowering and the flowering period determines the harvest time and the shipping time. Further in the case of green vegetables and edible roots or foliage plants, reduction in the yield or deterioration in the quality occurs due to flowering and therefore, very careful attention is paid to regulating flowering in cultivation.

Heretofore, the flowering properties of plants have been considered to be inherent to the species of plant. Artificial control of flowering has been effected by artificial control of the environment (sunshine duration or temperature). For doing so, it is required to use special facilities or change the location of cultivation. However, because of the expense involved with such measures, such requirements are not generally met. This results in problems for enlarging a production area and in yearlong cultivation, resulting in uneven production of farm products.

Thus, there remains a need for a method for regulating the flowering of plants in a simple manner and at low cost. There is also a need for plant growth regulators having a flowering regulatory activity.

SUMMARY OF THE INVENTION

Accordingly, it is an object of the present invention to provide a method for regulating the flowering of plants.

It is another object of the present invention to provide agents for regulating the flowering of plants.

These and other objects, which will become apparent in the course of the following detailed description, have been achieved by the inventors' discovery that protease inhibitors exhibit an activity of regulating the flowering of plants.

DETAILED DESCRIPTION OF THE PREFERRED EMBODIMENTS

Plants belonging to the family Lemnaceae are conventionally used for assaying substances for flowering regulatory activity.

In the plants belonging to the family Lemnaceae, the individual plants are small, growth rate is rapid and organic compounds such as sugar, etc. are absorbed readily, as compared to other plants. In addition, there are various members of the family requiring different conditions for inducing flowering. Furthermore, after flowering induction, the time period for determining differentiation of flower buds is also short. Thus, the plants belonging to the family Lemnaceae have excellent properties as a system for surveying flowering regulators.

It is known that flowering regulators generally function similarly in heterologous plants. In the case of, for example, a morning glory and a sweet potato, flowering can be induced in the sweet potato by grafting the sweet potato on the morning glory, which was induced to flower by a short-day treatment.

In view of such an example, it is considered that a flowering regulator having activity with the plants belonging to the family Lemnaceae will also exhibit activity as a general flowering regulator.

The plants belonging to the family Lemnaceae are classified in the genera Lemna, Spirodela, Wolffia and Wolffiella. Any plant belonging to the family Lemnaceae is suitable for surveying flowering regulators but *Lemna paucicostata* and *Lemna gibba* are preferably used.

In assaying flowering regulators using such plants belonging to the family Lemnaceae, various methods have been developed, but in general, the following method is used.

3-Frond colonies are cultured in a 50 ml Erlenmeyer flask charged with 25 ml of Hoagland type medium for duckweed and continuously exposed to light at 25° C. During the culture, a variety of substances are added to the medium or various treatments are made under nutrient conditions or under light conditions. Flower buds which are differentiated are observed one week after differentiation with a stereoscopic microscope and the influence of substances added or treatments on flowering is determined (for details of the present testing, see Examples).

The activity of protease inhibitors for inhibiting flowering has been found by the present inventors by adding to the medium for plants belonging to the family Lemnaceae a substance having such an activity. The protease inhibitors as used herein are protease inhibitors of from low molecular weight such as diisopropylfluorophosphoric acid (DFP), etc. to those of high molecular weight such as bestatin or soybean trypsin inhibitor and may also include inhibitors against serine protease, aspartic protease, thiol protease or metal protease. Inhibitors against serine protease are especially effective. Specific examples of protease inhibitors which are suitable for use in the present invention include, e.g., elastatinal, bestatin, DFP, 1-chloro-3-tosylamido-7-amino-L-2-heptanone

pepstatin, antipain, chymostatin, leupeptin, amastatin, (2S,3R)-3-amino-2-hydroxy-4-(4-nitrophenyl)-butanoyl-L-leucine hydrochloride, epiamastatin, and epibestatin. It is preferred that the protease inhibitor be bestatin.

The effect of the protease inhibitor can be sufficiently exhibited even at such a low concentration that no growth inhibition is observed at all. Furthermore, by choosing the protease inhibitor, flowering may be completely inhibited. Thus, the protease inhibitor may be suitably applied to the plant in an amount such that the protease inhibitor is present in the growth medium of the plant in an amount of 0.1 to 100 ppm, preferably 1 to 20 ppm, most preferably 2 to i0 ppm.

The protease inhibitor may be applied to the plant in any conventional manner such as, e.g., spraying. Although the exact amount will depend on the particular plant being treated, the protease inhibitor is suitably applied in an amount of 0.0001 kg/1000 m² to 100.0 kg/1000 m², preferably 0.001 kg/1000 m² to 10.0 kg/1000 m².

The protease inhibitor may be applied to the plants and/or soil as part of a flowering regulating composition, which contains a flowering regulating effective amount of the protease inhibitor and a carrier. Liquid compositions may suitably use water or an organic solvent as a carrier, while solid formulations may be prepared in granular form using talc or clays as inert carriers. The protease inhibitor is suitably contained in the flowering regulating composition in an amount of 0.001 to 90 wt. %, preferably 0.5 to 5 wt. %, based on the total weight of the composition. The composition may also contain an emulsifier o surface-active agent to potentiate the action of the protease inhibitor and influence the penetration, retention, surface tension, and drop size of the spray.

As stated above, the flowering of plants may be inhibited by applying the protease inhibitor to the plant. In particular, the present method may be used for controlling the flowering of green vegetables, such as cabbage and spinach, and chrysanthemums. By doing so, the present invention may contribute to stable production due to the lengthened cultivation period of green vegetables, because flowering and bolting of, for example, cabbages or spinaches cause a reduction in the harvest or a deterioration in the quality. Furthermore, in chrysanthemums which are cultivated under electric lighting to control production, production costs may be reduced by inhibiting flowering according to the present method instead of inhibiting flowering by night time lighting.

Other features of the invention will become apparent in the course of the following description of exemplary embodiments which are given for illustration of the invention and are not intended to be limiting thereof.

EXAMPLES

In this example, *Lemna paucicostata* 6746, the flowering of which was induced by a short-day treatment or, on an experimental scale, by exposure to far infrared light or a depletion of nitrogen components in the medium was used.

*Lemna paucicostata* was cultured at 25° C. in a 50 ml Erlenmeyer flask charged with 25 ml of Hoagland type medium (for the composition, see Table 1) improved for growing duckweed supplemented with a protease inhibitor in various concentrations. In culturing, the plant was irradiated with far infrared light for 3 consecutive days to induce flowering. Thereafter, the plant was cultured under continuous light. Table 2 shows the results obtained by adding as the protease inhibitor either elastatinal, bestatin, diisopropylfluorophosphoric acid (DFP), or CTAH. The data in Table 2 indicate the rate of the number of flowers per one thallus at each concentration to the number of flowers per one thallus when no protease inhibitor was added.

From the results, it is noted that the addition of the protease inhibitor effectively inhibits flowering. In particular, the effect of bestatin is remarkable, and flowering is fully prevented by adding only 1 ppm of bestatin. At this concentration, the growth was not affected at all.

TABLE 1

| Hoagland Type Medium for Growing Duckweed | | |
|---|---|---|
| $KH_2PO_4$ | 680 | mg/l |
| $KNO_3$ | 1515 | mg/l |
| $Ca(NO_3)_2 \cdot 4H_2O$ | 1180 | mg/l |
| $MgSO_4 \cdot 7H_2O$ | 492 | mg/l |
| $FeCl_3 \cdot 6H_2O$ | 5.4 | mg/l |
| $MnCl_2 \cdot 4H_2O$ | 3.62 | mg/l |
| $ZnSO_4 \cdot 7H_2O$ | 0.22 | mg/l |
| $CuSO_4 \cdot 5H_2O$ | 0.08 | mg/l |
| $Na_2MoO_4 \cdot 2H_2O$ | 0.12 | mg/l |
| $H_3BO_3$ | 2.86 | mg/l |
| Tartaric acid | 3.00 | mg/l |
| Sucrose | 10 | g/l |

TABLE 2

Effect of Protease Inhibitor on Inhibition of Flowering

| Protease Inhibitor | Concentration (ppm) | Flowering Rate as compared to control (%) |
|---|---|---|
| Elastatinal | 0 | 100.0 |
|  | 1 | 19.8 |
|  | 2 | 14.3 |
|  | 5 | 16.2 |
|  | 10 | 0.0 |
|  | 20 | 0.0 |
| Bestatin | 0 | 100.0 |
|  | 1 | 0.0 |
|  | 2 | 0.0 |
|  | 5 | 0.0 |
|  | 10 | 0.0 |
|  | 20 | 0.0 |
| DFP | 0 | 100.0 |
|  | 1 | 34.6 |
|  | 5 | 46.3 |
|  | 10 | 41.3 |
|  | 20 | 0.0 |
| CTAH | 0 | 100.0 |
|  | 0.5 | 90.8 |
|  | 1 | 81.4 |
|  | 2 | 76.2 |
|  | 5 | 17.1 |

Obviously, numerous modifications and variations of the present invention are possible in light of the above teachings. It is therefore to be understood that within the scope of the appended claims, the invention may be practiced otherwise than as specifically described herein.

What is claimed as new as desired to be secured by letters patent of the Unites States is:

1. A method for regulating the flowering of a plant, comprising treating a plant with a flowering regulating effective amount of a protease inhibitor selected from the group consisting of elastatinal, bestatin, diisopropylfluorophosphoric acid, CTAH and epibestatin.

2. The method of claim 1, wherein said plant is a plant belonging to the family Lemnaceae.

3. The method of claim 2, wherein said plant is a plant belonging to a genus selected from the group consisting of Lemna, Soirodela, Wolffia, and Wolffiella.

4. The method of claim 1, wherein said plant is selected from the group consisting of cabbage, spinach, and chrysanthemum.

5. The method of claim 5, wherein said protease inhibitor is bestatin.

6. The method of claim 1, wherein said protease inhibitor is present in the growth medium of said plant in an amount of from 0.1 to 100 ppm.

* * * * *

UNITED STATES PATENT AND TRADEMARK OFFICE
CERTIFICATE OF CORRECTION

PATENT NO. : 5,069,707
DATED : DECEMBER 3, 1991
INVENTOR(S) : GO TAKEBA ET AL

It is certified that error appears in the above-identified patent and that said Letters Patent is hereby corrected as shown below:

In column 2, line 65; "2 to io ppm" should read --2 to 10 ppm--;

In column 3, line 16; "emulsifier o surface-active" should read --emulsifier or surface-active--;

In claim 3, line 3; "Soirodela" should read --Spirodela--; and

In claim 5, line 1; "claim 5" should read --claim 1--.

Signed and Sealed this

Twenty-eighth Day of September, 1993

Attest:

Attesting Officer

BRUCE LEHMAN

Commissioner of Patents and Trademarks